United States Patent
Kamimura et al.

(10) Patent No.: US 6,479,532 B1
(45) Date of Patent: Nov. 12, 2002

(54) ANTIFUNGAL COMPOSITIONS

(75) Inventors: Toshiaki Kamimura, Ibaraki (JP); Tsuguo Yabuta, Ibaraki (JP); Saburo Obata, Ibaraki (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/926,334

(22) PCT Filed: Apr. 13, 2000

(86) PCT No.: PCT/JP00/02402

§ 371 (c)(1),
(2), (4) Date: Oct. 15, 2001

(87) PCT Pub. No.: WO00/62776

PCT Pub. Date: Oct. 26, 2000

(30) Foreign Application Priority Data

Apr. 16, 1999 (JP) ............................................. 11-108753
Dec. 28, 1999 (JP) ............................................. 11-371993

(51) Int. Cl.$^7$ ............................................. A61K 31/415
(52) U.S. Cl. ....................................... 514/397; 514/427
(58) Field of Search ................................... 514/427, 397

(56) References Cited

FOREIGN PATENT DOCUMENTS

| EP | 170139 | * | 2/1986 | ......... A61K/31/415 |
| JP | 7-309755 | * | 11/1995 | ......... A61K/31/415 |

* cited by examiner

*Primary Examiner*—James H. Reamer
(74) *Attorney, Agent, or Firm*—Oblon, Spivak, McClelland, Maier & Neustadt, P.C.

(57) ABSTRACT

This invention relates to an antimycotic composition comprising pyrrolnitrin and at least one member selected from the group consisting of lanoconazole, butenafine or a salt thereof, and an allylamine-series antimycotic agent as active ingredients, which composition has a potent antimycotic action as compared with its component drugs used each independently and is not only of great use in the treatment of dermatophytosis such as tinea, *tinea imbricata, tinea favosa, tinea profunda,* etc. and fungal infections such as candidiasis of *cutaneous mucosa, candidiasis profunda,* etc. but also useful from the standpoint of alleviation of side effects and improvement in the patient's compliance.

21 Claims, No Drawings

ANTIFUNGAL COMPOSITIONS

TECHNICAL FIELD

This invention relates to an antimycotic composition comprising pyrrolnitrin and at least one member selected from the group consisting of lanoconazole, butenafine or a salt thereof, and an allylamine-series antimycotic agent as active ingredients and, as such, finds application in the field of medical care.

BACKGROUND ART

Pyrrolnitrin is a drug having antimycotic activity which is represented by the chemical formula (1) given hereunder and has been used widely in a single-agent regimen or a-multiple-agent regimen including other antimycotic drugs.

Referring to the above multiple-agent regimen, there is known an antimycotic composition comprising pyrrolnitrin and an imidazole-series antimycotic agent, such as clotrimazole, as active ingredients (JP Kokai S61-56127).

Meanwhile, lanoconazole, butenafine, and terbinafine, an allylamine-series antimycotic agent, which are represented by the hereunder-given chemical formulas (2)~(4), respectively, are invariably drugs having antifungal activity and have been used in single-agent regimens.

However, there is not known any antimycotic composition comprising pyrrolnitrin and at least one member selected from the group consisting of lanoconazole, butenafine or a salt thereof, and terbinafine, which is an allylamine-series antimycotic agent, or a salt thereof as active ingredients.

While the above-mentioned antimycotic drugs each used alone display excellent antimycotic activity, development of a more potent antimycotic drug has been awaited for alleviation of side effects, improvement in the patient's compliance, and reduction in the cost of active substance bulk.

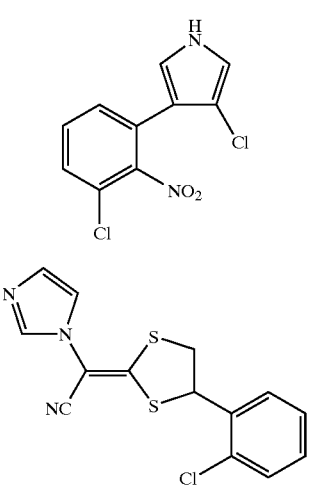

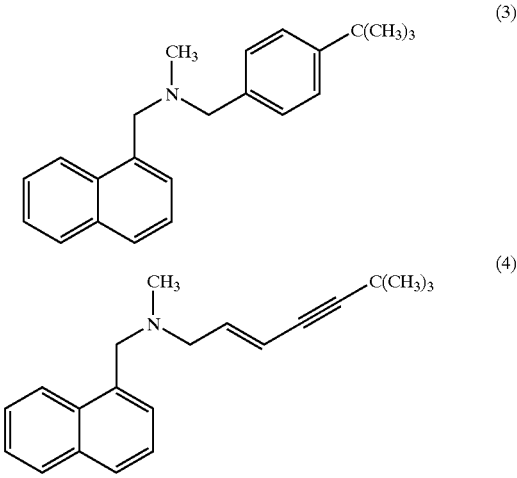

DISCLOSURE OF INVENTION

The inventors of this invention found that the combined use of pyrrolnitrin and lanoconazole, the combined use of pyrrolnitrin and butenafine or a salt thereof, and the combined use of pyrrolnitrin and an allylamine-series antimycotic agent, particularly terbinafine or a salt thereof, respectively result in a synergistic effect as compared with the effect of any of these drugs used independently, thus providing an antimycotic composition having potentiated antimycotic and fungicidal activities.

The antimycotic composition of this invention is characterized by comprising pyrrolnitrin and at least one member selected from the group consisting of lanoconazole, butenafine or a salt thereof, and an allylamine-series antimycotic agent as active ingredients.

Preferably, the antimycotic composition of this invention is characterized by comprising pyrrolnitrin and lanoconazole as active ingredients.

Also preferably, the antimycotic composition of this invention is characterized by comprising pyrrolnitrin and butenafine or a salt thereof.

The salt of butenafine for use in the above antimycotic composition of the invention includes the hydrochloride, among others.

Further preferably, the antimycotic composition of this invention is characterized by comprising pyrrolnitrin and an allylamine-series antimycotic agent.

The allylamine-series antimycotic agent for use in the above antimycotic composition of this invention is preferably terbinafine or a salt thereof.

The salt of terbinafine may for example be the hydrochloride.

BEST MODE FOR CARRYING OUT THE INVENTION

The ratio by weight of pyrrolnitrin to lanoconazole, that of pyrrolnitrin to butenafine or its salt, and that of pyrrolnitrin to the allylamine-series antimycotic agent in the specific antimycotic compositions of the invention are invariably 10:1~1:10, preferably 5:1~1:5, more preferably 2:1~1:2, and the ratio should be adjusted according to the type of antimycotic drug, the target pathogenic microorganism, the severity of illness, and other variables.

The dosage, as active substance, of said antimycotic compositions of the invention can be judiciously selected according to the dosage form, the ratio of active ingredients, the pathogenic microorganism to be dealt with, and severity of illness, among other variables, but generally these antimycotic compositions are respectively administered within the dose range of 0.01~10 mg/day, preferably 0.05~5 mg/day.

In addition to the above-mentioned active ingredients, each antimycotic composition of the invention may contain suitable amounts of an antipruritic, antiinflammatory, analgesic or local anesthetic agent, such as crotamiton, diphenhydramine, lidocaine, dibucaine, methyl salicylate, menthol, camphor, glycyrrhetinic acid, azulene, etc.; biocides, such as benzalkonium chloride, benzethonium chloride, chlorhexidine, phenol, chlorobutanol, iodine, etc.; a keratolytic or emolient, such as salicylic acid, diethyl sebacate, urea, sulfur, etc.; and/or an astringent or tissue-repairing agent, such as zinc chloride, allantoin, etc.

The dosage form for the antimycotic composition of this invention is not particularly restricted. Preferably, however, it includes various dosage forms for external application which are similar to those of hitherto-known antimycotic drugs, thus including solutions, gels, creams, ointments, aerosols, dusts, vaginal suppositories and so forth.

The antimycotic composition of this invention can be formulated with various pharmaceutical bases or carriers such as those mentioned below and, then, processed into the above dosage forms by the routine procedures, for example the protocols described in The Pharmacopoeia of Japan XIII.

To mention a few examples, vaseline, white wax, paraffin, polyethylene glycol, etc. can be formulated when the composition is to be molded into ointments; oils and fats, higher fatty acids, higher alcohols, fatty acid esters, purified water, polyhydric alcohols, emulsifiers, etc. can be added for the preparation of creams; carboxyvinyl polymers, water-soluble basic substances (alkali hydroxides, etc.), hydroxypropylcellulose, hydroxypropylmethylcellulose, polyvinyl alcohol, polyvinylpyrrolidone, purified water, lower alcohols, polyhydric alcohols, polyethylene glycol, etc. can be added for the preparation of gels; and lower alcohols, glycerol, propylene glycol, purified water, etc. can be added for the preparation of solutions.

The following test examples illustrate the effect of the antimycotic composition of this invention.

TEST EXAMPLE 1

The Synergistic Effect of a Combination of Pyrrolnitrin (Hereinafter Referred to Sometimes as "PY") and Lanoconazole (Hereinafter "LC")

1. Test Organisms
   a: *Candida albicans* YU-1200
   b: *Candida albicans* 12012
   c: *Trichophyton rubrum* 7030
   d: *Trichophyton rubrum* 7010
2. Test Medium
   Sabouraud's glucose agar (glucose 2%)
3. Preparation of Test Microbial Suspensions
   With Trichophyton spp., each strain was cultured on a Sabouraud's glucose agar (glucose 2%) slant at 25° C. for 2~3 weeks. Then, about 3~5 ml of physiological saline supplemented with 0.1% (w/v) Tween 80 and sterilized was added to the above slant culture of the test strain and conidia were liberated by scratching the slant surface with a platinum loop. The collected conidial suspension was filtered through a fine-mesh metal sieve to remove hyphal masses and, then, centrifuged at 3000×g for 10 minutes to concentrate the conidia. The concentrate was resuspended in the same sterile saline solution as above, the conidia were counted with a hemocytometer, and the suspension was adjusted to a predetermined conidial population ($10^5$ spores/ml).

*Candida albicans* was cultured in Sabouraud's broth medium (glucose 2%) at 30° C. for 24 hours and the resulting culture was diluted 10-fold with the same medium as above ($10^5$ cells/ml) and used.

4. Drugs Used
   Using ethyl alcohol for PY and dimethyl sulfoxide (DMSO) for LC, a 1 mg/ml solution of each drug was respectively prepared. Then, the solution was diluted to a predetermined concentration using 20% ethyl alcohol as diluent for PY and 10% DMSO as diluent for LC.
5. Evaluation of the Effect of Each Combination Drug by Agar Plate Dilution Assay
   For the determination of inhibitory activity, 0.5 ml of a PY solution and 0.5 ml of an LC solution, each adjusted to a predetermined concentration were blended with 9 ml of Sabouraud's glucose agar medium to prepare drug-containing plates (checker board method).

Each plate was inoculated with a microbial suspension of predetermined concentration (cells or spores/ml) by the stamping method. Trichophyton spp. were cultured at 25° C. for 2 weeks and Candida spp. were cultured at 30° C. for 2 days. Then, the growth of each test strain was investigated.

The FIC index was calculated from the MIC value of PY or LC as used alone or PY and LC as used in combination.

The results are shown in Table 1.

TABLE 1

| | MIC ($\mu$g/ml) | | FIC index in parentheses |
|---|---|---|---|
| Test strain | PY alone | LC alone | PY + LC |
| a | 12.5 | 12.5 | 0.78 + 0.78 (0.125) |
| b | 25 | 25 | 0.78 + 1.56 (0.094) |
| c | 0.2 | 0.0125 | 0.025 + 0.00625 (0.625) |
| d | 0.2 | 0.025 | 0.025 + 0.00625 (0.375) |

TEST EXAMPLE 2

The Fungicidal Effect of a 1:1 Combination of PY and LC (Experimental Conditions)
   Medium used: Sabouraud's (glucose 2%) broth medium
   Test strain: *Candida albicans* 12012
   Inoculum size: about $10^4$ cells/ml (1% of a 24-hour culture using Sabouraud's broth medium at 30° C.)

(Test Method)
   To one part by volume of a drug solution prepared at a concentration 10 times the predetermined concentration was added 9 parts by volume of the inoculated Sabouraud's broth medium, followed by mixing. The mixture was incubated at 30° C. for 24 hours and the MIC was determined.

Furthermore, 0.1 ml samples were taken from the test microbial suspensions of varying concentrations and inoculated onto Sabouraud's (glucose 2%) agar plates using Conradi's spreader.

After 2 days of culture at 30° C., the colonies formed were counted and the number of remaining viable cells per 0.1 ml was determined.

The viable cell counts thus found are shown in Table 2.

TABLE 2

Viable cell count (CFU/0.1 ml) (∞: 10³~10⁴

| Drug concentration (μg/ml) | PT alone | LC alone | PY + LC (1:1) |
|---|---|---|---|
| 3.13 | ∞ | ∞ | 276 |
| 6.25 | ∞ | ∞ | 31 |
| 12.5 | 1012 | 876 | 16 |
| 25 | 1 | 308 | 19 |

The results of Test Example 1 indicate that the antimycotic composition comprising PY and LC according to this invention shows a potent synergistic inhibition of the test organisms.

Moreover, the results of Test Example 2 indicate that the antimycotic composition comprising PY and LC according to this invention exhibits higher fungicidal activity at low concentration as compared with each of the component drugs used alone.

TEST EXAMPLE 3

The Synergistic Effect of a Combination of Pyrrolnitrin (Hereinafter Referred to Sometimes Briefly as "PY") and Butenafine Hydrochloride (Hereinafter Referred to Sometimes as "BTF")

1. Test Organisms
   e: *Trichophyton rubrum* 7005
   f: *Trichophyton rubrum* 7030
   g: *Staphylococcus epidermidis* 15001

2. Test Medium

For Trichophyton spp., the same medium as used in Test Example 1 was used.

For the general bacterium (*S. epidermidis*), Mueller Hinton agar medium was used.

3. Preparation of Test Microbial Suspensions

With Trichophyton spp., the procedure of Test Example 1 was repeated.

The general bacterium was cultured in Mueller Hinton broth medium at 37° C. for 20 hours and the culture was diluted 100-fold with the same medium (10⁶ cells/ml) and used.

4. Drugs Used

A 1 mg/ml solution of each drug was prepared by using ethyl alcohol for PY or dimethyl sulfoxide (DMSO) for BTF and diluted to a predetermined concentration using 20% ethyl alcohol as diluent for PY or 10% DMSO as diluent for BTF.

5. Evaluation of the Effect of Each Combination Drug by Agar Plate Dilution Assay In the case of Trichophyton spp., 0.5 ml of a PY solution and 0.5 ml of a BTF solution, both of predetermined concentration, were blended with 9 ml of the medium to prepare a drug-containing agar plate and the procedure of test Example 1 was repeated.

In the case of the general bacterium, Mueller Hinton agar medium was used to prepare plates and the procedure of Test Example 1 was repeated. After 20 hours of culture at 37° C., the growth of the test organism was investigated.

Calculation of the FIC index was also performed in the same manner as in Test Example 1.

The results are shown in Table 3.

TABLE 3

| | MIC (μg/ml) | | FIC index in parentheses |
|---|---|---|---|
| Test strain | PY alone | BTF alone | PY + BTF |
| e | 0.1 | 0.025 | 0.025 + 0.00625 (0.500) |
| f | 0.1 | 0.025 | 0.025 + 0.00625 (0.500) |
| g | 25 | 25 | 3.13 + 3.13 (0.250) |

The results of Test Example 3 indicate that the antimycotic composition comprising PY and BTF according to this invention exhibits a potent synergistic inhibition of the test organisms.

TEST EXAMPLE 4

The Synergistic Effect of a Combination of Pyrrolnitrin (Hereinafter Referred to Sometimes as "PY") and Terbinafine Hydrochloride (Hereinafter Referred to Sometimes as "TF")

1. Test Organisms
   h: *Candida albicans* 16010
   i: *Trichophyton rubrum* 7010
   j: *Trichophyton rubrum* 7030
   k: *Staphylococcus aureus* FP5
   l: *Staphylococcus epidermidis* 15001

2. Test Medium

Mueller Hinton agar medium was used for Staphylococcus spp. and Sabouraud's glucose agar (glucose 2%) medium was used for the fungi.

3. Preparation of Test Microbial Suspensions

With Trichophyton spp., each strain was cultured on a Sabouraud's glucose agar (glucose 2%) slant at 25° C. for 2~3 weeks. Then, about 3~5 ml of physiological saline supplemented with 0.1% (w/v) Tween 80 and sterilized were added to the above slant culture of the test strain and conidia were liberated by scratching the slant surface with a platinum loop. The collected conidial suspension was filtered through a fine-mesh metal sieve to remove hyphal masses and, then, centrifuged at 3000×g for 10 minutes to concentrate the conidia. The concentrate was resuspended in the same sterile saline solution as above, the conidia were counted with a hemocytometer, and the suspension was adjusted to a predetermined conidial population (10⁵ spores/ml).

*Candida albicans* was cultured in Sabouraud's broth medium (glucose 2%) at 30° C. for 24 hours and the culture was diluted 10-fold (10⁵ cells/ml) with the same medium and used.

Staphylococcus spp. were cultured in Mueller Hinton broth medium at 37° C. for 18~20 hours and diluted 100-fold with the same medium (about 10⁶ cells/ml) and this dilution was used as the inoculum.

4. Drugs Used

A 1 mg/ml solution of each drug was prepared using ethyl alcohol for PY or dimethyl sulfoxide (DMSO) for TF and diluted to a predetermined concentration by using 20% ethyl alcohol as diluent for PY or 10% DMSO as diluent for TF.

5. Evaluation of the Effect of Each Combination Drug by Agar Plate Dilution Assay For the determination of the growth-inhibitory effects of drugs on test organisms, drug-containing plates were prepared by blending 0.5 ml of a PY solution and 0.5 ml of a TF solution, both of predetermined concentration, with 9 ml of said medium.

The plates were inoculated with the microbial suspensions (cells or spores/ml) by the stamping technique. Trichophyton spp. were cultured at 25° C. for 2 weeks, Candida spp. at 30° C. for 2 days, and Staphylococcus spp. at 37° C. for 20 hours. Then, the growth of each test organism was investigated (checker board method).

The FIC index was calculated from the MIC value of PY or TF alone or the two drugs used in combination.

The results are shown in Table 4.

TABLE 4

| Test organism | MIC (µg/ml) | | FIC index in parentheses |
|---|---|---|---|
| | PY alone | TF alone | PY + TF |
| h | 25 | 50 | 6.25 + 1.56 (0.281) |
| i | 0.2 | 0.0125 | 0.05 + 0.00313 (0.5) |
| j | 0.39 | 0.0125 | 0.1 + 0.00313 (0.5) |
| k | 25 | 50 | 12.5 + 6.25 (0.625) |
| l | 12.5 | 25 | 6.25 + 3.13 (0.625) |

The results of Test Example 4 indicate that the antimycotic composition comprising PY and TF according to this invention shows a potent synergistic inhibition of the test organisms.

EXAMPLE 1

| | |
|---|---|
| Pyrrolnitrin | 2.5 g |
| Lanoconazole | 1.0 g |
| Glycerol | 50 g |
| Ethanol | 300 ml |
| Purified water | q.s. |

Pyrrolnitrin (2.5 g) and lanoconazole (1 0 g) were dissolved in glycerol (50 g)-ethanol (300 ml), followed by addition of purified water to make 1000 ml. This mixture was homogenized by stirring to give a solution for external application.

EXAMPLE 2

| | |
|---|---|
| Pyrrolnitrin | 2.5 g |
| Butenafine hydrochloride | 5.0 g |
| White petrolatum | 200 g |
| Stearyl alcohol | 200 g |
| Propylene glycol | 100 g |
| Sodium lauryl sulfate | 15 g |
| Methyl paraben | 0.2 g |
| Propyl paraben | 0.2 g |
| Purified water | q.s. |

Pyrrolnitrin (2.5 g), butenafine hydrochloride (5.0 g) and propyl paraben (0.2 g) were dissolved in white petrolatum (200 g)-stearyl alcohol (200 g)-propylene glycol (100 g) under warming and stirring.

On the other hand, sodium lauryl sulfate (15 g) and methyl paraben (0.2 g) were dissolved in purified water under warming. To this solution was added the active drug solution prepared above and the mixture was emulsified by stirring to give an ointment (1000 g).

EXAMPLE 3

| | |
|---|---|
| Pyrrolnitrin | 2.5 g |
| Butenafine hydrochloride | 2.5 g |
| Glycerol | 50 g |
| Ethanol | 300 mg |
| Purified water | q.s. |

The above ingredients were treated as in Example 1 to give 1000 ml of a solution for external application.

EXAMPLE 4

| | |
|---|---|
| Pyrrolnitrin | 2.5 g |
| Lanoconazole | 2.5 g |
| White petrolatum | 200 g |
| Stearyl alcohol | 200 g |
| Propylene glycol | 100 g |
| Sodium lauryl sulfate | 15 g |
| Methyl paraben | 0.2 g |
| Propyl paraben | 0.2 g |
| Purified water | q.s. |

The above ingredients were treated as in Example 2 to give 1000 g of an ointment.

EXAMPLE 5

| | |
|---|---|
| Pyrrolnitrin | 2.5 g |
| Terbinafine hydrochloride | 5.0 g |
| Glycerol | 50 g |
| Ethanol | 300 ml |
| Purified water | q.s. |

Pyrrolnitrin (2.5g) and terbinafine hydrochloride (5.0 g) were dissolved in glycerol (50 g)-ethanol (300 ml) , followed by addition of sufficient purified water to make 1000 ml. The mixture was stirred well to give a solution for external application.

EXAMPLE 6

| | |
|---|---|
| Pyrrolnitrin | 2.5 g |
| Terbinafine hydrochloride | 1.0 g |
| White petrolatum | 200 g |
| Stearyl alcohol | 200 g |
| Propylene glycol | 100 g |
| Sodium lauryl sulfate | 15 g |
| Methyl paraben | 0.2 g |
| Propyl paraben | 0.2 g |
| Purified water | q.s. |

Pyrrolnitrin (2.5 g), terbinafine hydrochloride (1.0 g) and propyl paraben (0.2 g) were dissolved in white petrolatum (200 g)-stearyl alcohol (200 g)-propylene glycol (100 g) under warming and stirring.

On the other hand, sodium lauryl sulfate (15 g) and methyl paraben (0.2 g) were dissolved in purified water under warming. To this solution was added the above active drug solution, and the mixture was emulsified by thorough stirring to give an ointment (1000 g).

INDUSTRIAL APPLICABILITY

As described above, the antimycotic composition of this invention is of great use for the therapy of dermatophytosis such as tinea, *tinea imbricata, tinea favosa, tinea profunda,* etc. and fungal infections such as candidiasis of *cutaneous mucosa, candidiasis profunda,* and so forth.

Furthermore, the antimycotic composition of this invention produces marked antimycotic effects as compared with its component drugs used each independently and is of great use from the standpoint of alleviation of side effects and improvement in the patient's compliance.

What is claimed is:

1. A composition comprising an antimycotic amount of:
   (a) pyrrolnitrin and
   (b) at least one compound or salt thereof selected from the group consisting of lanoconazole, betenafine and an allylamine-series antimycotic agent.

2. A composition comprising an antimycotic amount of:
   (a) pyrrolnitrin and (b) lanoconazole or a salt thereof.

3. A composition of comprising and antimycotic amount of:
   (a) pyrrolnitrin and (b) betenafine or a salt thereof.

4. A composition of comprising an antimycotic amount of:
   (a) pyrrolnitrin and (b) an allylamine-series antimycotic agent or a salt thereof.

5. The composition of claim 4 that comprises terbinafine or a salt thereof as the allylamine-series agent.

6. The composition of claim 1 wherein the weight ratio of (a) to (b) ranges from 10:1 to 1:10.

7. The composition of claim 1 wherein the weight ratio of (a) to (b) ranges from 5:1 to 1:5.

8. The composition of claim 1 wherein the weight ratio of (a) to (b) ranges from 2:1 to 1:2.

9. The composition of claim 1 further comprising one or more antipruritic, anti-inflammatory, analgesic, or local anesthetic agent(s).

10. The composition of claim 1 further comprising one or more biocide(s).

11. The composition of claim 1 further comprising one or more keratolytic agent(s) or emollient(s), or both.

12. The composition of claim 1 further comprising one or more astringent(s).

13. The composition of claim 1 further comprising one or more tissue-repairing agent(s).

14. The composition of claim 1 in the form of a solution or suppository.

15. The composition of claim 1 in the form of a gel, cream or ointment.

16. The composition of claim 1 in the form of an aerosol or dust.

17. The composition of claim 1 further comprising one or more pharmaceutical base(s) or carrier(s).

18. A method for treating a mycotic infection comprising administering a dose of the composition of claim 1 effective to treat said mycotic infection to a subject in need thereof.

19. The method of claim 18 comprising treating a Candida infection.

20. The method of claim 18 comprising treating a Trichophyton infection.

21. A method for making an anti-mycotic composition comprising mixing or compounding
   (a) pyrrolnitrin with
   (b) at least one compound or salt thereof selected from the group consisting of lanoconazole, betenafine and an allylamine-series antimycotic agent.

* * * * *